(12) United States Patent
Kawaguchi et al.

(10) Patent No.: US 7,935,673 B2
(45) Date of Patent: May 3, 2011

(54) POLYPHENOL GLYCOSIDE ISOLATED FROM ACEROLA

(75) Inventors: Masakazu Kawaguchi, Higashimurayama (JP); Kenichi Nagamine, Higashimurayama (JP)

(73) Assignee: Nichirei Biosciences, Inc., Tokyo (JP)

( * ) Notice: Subject to any disclaimer, the term of this patent is extended or adjusted under 35 U.S.C. 154(b) by 662 days.

(21) Appl. No.: 11/722,211

(22) PCT Filed: Dec. 12, 2005

(86) PCT No.: PCT/JP2005/022755
§ 371 (c)(1),
(2), (4) Date: Jun. 20, 2007

(87) PCT Pub. No.: WO2006/067985
PCT Pub. Date: Jun. 29, 2006

(65) Prior Publication Data
US 2010/0029918 A1    Feb. 4, 2010

(30) Foreign Application Priority Data

Dec. 22, 2004  (JP) ................. 2004-372266

(51) Int. Cl.
*A01N 43/04* (2006.01)
*A61K 31/70* (2006.01)
*C07H 15/00* (2006.01)
*C07H 17/00* (2006.01)

(52) U.S. Cl. .......................... 514/27; 536/8
(58) Field of Classification Search .................. None
See application file for complete search history.

(56) References Cited

U.S. PATENT DOCUMENTS

| 7,074,907 B2 * | 7/2006 | Nagamine et al. | 536/18.2 |
| 7,090,872 B2 * | 8/2006 | Nagamine et al. | 424/725 |
| 7,192,617 B2 * | 3/2007 | Nagamine et al. | 424/776 |

FOREIGN PATENT DOCUMENTS

| JP | 02-200610 A | 8/1990 |
| JP | 05-344846 A | 12/1993 |
| JP | 2000-212026 A | 8/2000 |
| JP | 2000-212027 | * 8/2000 |
| JP | 2000-212027 A | 8/2000 |
| JP | 2000-212032 A | 8/2000 |
| JP | 2000-270807 A | 10/2000 |
| JP | 2004-175856 A | 6/2004 |
| JP | 2005-082509 A | 3/2005 |
| JP | 2005-139093 A | 6/2005 |
| JP | 2005-154432 A | 6/2005 |
| JP | 2005-263726 A | 9/2005 |
| JP | 2005-320262 A | 11/2005 |

OTHER PUBLICATIONS

Byrn et al. Solid-State Chemistry of Drugs, 2d, Chapter 11 Hydrates and Solvates, 233-247, 1999.*
Morissette et al. Adv. Drug Delivery Rev. 2004, 56, 275-300.*
Kayo Doi, et al.; "Studies on the Constituents of the Leaves of *Morus alba* L."; XP-001148950; Chemical and Pharmaceutical Bulletin, Pharmaceutical Society of Japan; Feb. 2001; pp. 151-153; vol. 49, No. 2; Japan.
Takayuki Hanamura, et al.; "Structural and Functional Characterization of Polyphenols Isolated from Acerola (*Malpighia emarginata* D.C.) Fruit"; Biosci. Biotechnol. Biochem.; 2005; pp. 280-286; vol. 69; No. 2; Japan.
Takayuki Hanamura, et al.; "Effect of Suppressing Increases in Blood Sugar Levels Found in Polyphenol Fractions Derived from Acerola (*Malpighia emarginata* D.C.) Fruits"; Lecture Abstracts of Annual Meeting of JSBBA 2005 (Sapporo, Japan); Mar. 5, 2005; p. 106; Japan.
Eriko Uchida, et al.; "Effect of Suppressing Melanin Formation Found in Polyphenols Derived from Acerola (*Malpighia emarginata* D.C.) Fruits"; Lecture Abstracts of Annual Meeting of JSBBA 2005 (Sapporo, Japan); Mar. 5, 2005; p. 103; Japan.
Japanese Notice of Rejection dated Mar. 2, 2010, issued in Japanese Patent Application No. 2004-372266.

* cited by examiner

*Primary Examiner* — Traviss C McIntosh, III
(74) *Attorney, Agent, or Firm* — Sughrue Mion, PLLC (57) ABSTRACT

It is an objective of the present invention to provide a polyphenol glycoside isolated from acerola, which has a binding mode that has not been conventionally known, and to provide the use of the same.
The present invention relates to a compound represented by formula (I):

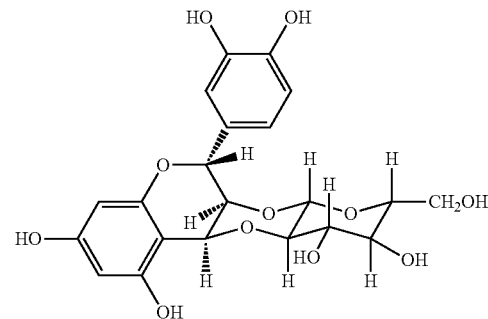

and an antioxidant, a glucosidase inhibitor, a food, a cosmetic, and a skin preparation for external use, each of which comprises such compound.

8 Claims, 9 Drawing Sheets

POLYPHENOL GLYCOSIDE ISOLATED FROM ACEROLA

TECHNICAL FIELD

The present invention relates to a novel polyphenol glycoside, a method for producing the same, and the use of the same.

BACKGROUND ART

An example of a known polyphenol glycoside is quercetin-3-glucoside (isoquercitrin), represented by the following formula (Non-Patent Document 1):

In such glycoside, a sugar is bound to the carbon at position 3 of quercetin via glycosidic linkage. However, glycoside in which a sugar is bound to the carbon at position 4 of quercetin via glycosidic linkage has not been known.

Known examples of a polyphenol compound analogous to quercetin include dehydroquercetin (taxifolin):

and leucocyanidin:

It has been known that, in plants, hydrogen binds to oxygen bound to the carbon at position 4 of dehydroquercetin, resulting in the generation of leucocyanidin and leading to the generation of cyanidin from leucocyanidin. That is, dehydroquercetin and leucocyanidin are intermediates used for cyanidin synthesis. Also, regarding dehydroquercetin and leucocyanidin, no glycoside in which a sugar is bound to the carbon at position 4 via a glycosidic linkage has been known.

Meanwhile, in accordance with changes in dietary habits and lifestyle of recent years, the number of diabetic patients is increasing. At present, the number of diabetic patients is as high as 7,000,000 in Japan, and such number could be as large as 15,000,000 when future diabetics are added. Diabetes is a metabolic disorder in which a prolonged hyperglycemic state caused by an insufficient level of insulin hormone activities is exhibited. A prolonged hyperglycemic state may result in development of various types of complications, such as nervous disorders, cataracts, renal disorders, retinopathy, arthrosclerosis, atherosclerosis, and diabetic gangrene.

Thus, inhibition of increases in blood sugar levels is thought to be involved in a method for treating or preventing diabetes. In this regard, many medical agents for treating and preventing diabetes and diabetic complications have so far been developed.

Examples of such medical agents include an α-glucosidase inhibitor that inhibits digestion and absorption of carbohydrates to prevent the blood glucose level from becoming elevated. Voglibose and acarbose are known as representative α-glucosidase inhibitors.

While these agents have remarkable effects, they impose various side effects on patients, such as a feeling of fullness upon ingestion, induction of a hypoglycemic state due to the combined use thereof with other hypoglycemic agents, and nausea or headache. In order to overcome such drawbacks, agents made from natural ingredients, which have mild effects and are free from problems related to side effects, have been developed. For example, an extract of Japanese basil (Patent Document 1), an extract of yerba mate leaves (Patent Document 2), an extract of *Apocynum venetum* leaves (Patent Document 3), and an extract of eriobotryae folium (Patent Document 4), are known as α-glucosidase inhibitors made from natural ingredients, although the number of such agents that have been provided is not sufficiently large.

Meanwhile, active oxygen has been known to have adverse influences upon living bodies. Examples of such adverse influences upon living bodies include aging, carcinogenesis, and development of blemishes or freckles. In addition, active oxygen has been known to cause deterioration of cosmetics, beverages, and foods. As an antioxidant that removes active oxygen, ascorbic acid (vitamin C) or the like is used in cosmetics, beverages, and foods. In recent years, an antioxidant with improved safety that is derived from a natural product has been awaited.

Patent Document 1: JP Patent Publication (Kokai) No. 2000-102383 A
Patent Document 2: JP Patent Publication (Kokai) No. 2003-146900 A
Patent Document 3: JP Patent Publication (Kokai) No. 2002-053486 A
Patent Document 4: JP Patent Publication (Kokai) No. 2003-128571 A
Non-Patent Document 1: Chem. Pharm. Bull. 49 (2)151-153 (2001)

DISCLOSURE OF THE INVENTION

It is an objective of the present invention to provide a polyphenol glycoside being isolated from acerola and having a binding mode that has not been conventionally known, and to provide the use of the same.

The present invention encompasses the following inventions.

(1) A compound represented by the following formula (I):

a salt thereof, or a solvate of either thereof.

(2) A glucosidase inhibitor comprising, as an active ingredient, the compound represented by formula (I) according to (1), a salt thereof, or a solvate of either thereof.

(3) An antioxidant comprising, as an active ingredient, the compound represented by formula (I) according to (1), a salt thereof, or a solvate of either thereof.

(4) A food comprising the compound represented by formula (I) according to (1), a salt thereof, or a solvate of either thereof.

(5) A cosmetic comprising the compound represented by formula (I) according to (1), a salt thereof, or a solvate of either thereof.

(6) A skin preparation for external use comprising the compound represented by formula (I) according to (1), a salt thereof, or a solvate of either thereof (note that the term "skin preparation for external use" used herein is not limited to drugs and encompasses quasi-drugs, general skin cosmetics, medical cosmetics, and the like).

(7) A method for producing the compound represented by formula (I) according to (1), comprising isolating the compound from an acerola fruit or a processed product thereof.

According to the present invention, a method for treating or preventing diabetes, comprising administering the compound represented by formula (I), a salt thereof, or a solvate of either thereof in an amount effective for treatment or prevention of diabetes to a patient who needs treatment or prevention of diabetes is provided.

According to the present invention, a method for treating or preventing diseases in which active oxygen is involved (e.g., skin diseases, aging, ischemic diseases, arteriosclerosis, nephritis, and cancers), comprising administering the compound represented by formula (I), a salt thereof, or a solvate of either thereof in an amount effective for treatment or prevention of the aforementioned diseases to a patient who needs treatment or prevention of the diseases is provided.

According to the present invention, a method for preventing or improving skin disorders in which active oxygen is involved (e.g., blemishes and freckles), comprising applying the compound represented by formula (I), a salt thereof, or a solvate of either thereof to the skin of a human is provided.

According to the present invention, the use of the compound represented by formula (I), a salt thereof, or a solvate of either thereof for producing a glucosidase inhibitor (i.e., a therapeutic agent for diabetes), an antioxidant (i.e., a therapeutic agent for a disease in which active oxygen is involved), or a food or cosmetic having glucosidase inhibitory activity or antioxidative activity is provided.

Effects of the Invention

According to the present invention, a novel polyphenol glycoside is provided. Such compound has high levels of antioxidative activity and glucosidase inhibitory activity.

This description includes part or all of the contents as disclosed in the description of Japanese Patent Application No. 2004-372266, which is a priority document of the present application.

BEST MODE FOR CARRYING OUT THE INVENTION

The compound (novel polyphenol glycoside) of the present invention has a characteristic binding mode in which glucose is bound to both the carbon at position 3 and the carbon at position 4 of polyphenol (taxifolin) via a glycosidic linkage. Such binding mode has not been conventionally known.

The novel polyphenol glycoside of the present invention may exist in the form of a salt. Preferably, it may exist in the form of a pharmaceutically acceptable salt. Examples of such salt include pharmaceutically acceptable nontoxic salts, including: alkali metal salts or an alkaline earth metal salt such as a sodium salt, a potassium salt, and a calcium salt; hydrogen halide salts such as hydrochloride; inorganic acid salts such as nitrate, sulfate, and phosphate; sulfonates such as methansulfonic acid and benzenesulfonic acid; organic acid salts such as fumaric acid, succinic acid, citric acid, oxalic acid, and maleic acid; and amino acid salts such as glutamic acid and aspartic acid.

The novel polyphenol glycoside of the present invention may exist in the form of a solvate. Preferred examples of such solvate include hydrate and ethanolate.

As a result of a radical scavenging activity test with the use of a DPPH reagent, it has been revealed that the novel polyphenol glycoside of the present invention has radical scavenging activity almost comparable to that of α-tocopherol (vitamin E). Oxidation in living bodies has been known to be induced by free radicals generated from oxygen, lipids, and the like. The strength of such radical scavenging action is related to the strength of antioxidative activity. Vitamin E is oil-soluble and insoluble in water. However, the polyphenol glycoside of the present invention has structures of hydrophobic phenolic group and hydrophilic glucose. Thus, the polyphenol glycoside of the present invention is expected to be used in various applications.

Also, the polyphenol glycoside of the present invention is useful as a glucosidase inhibitor. Hitherto, it has been revealed that isoquercitrin has high glucosidase inhibitory activity among acerola-derived polyphenol components. The polyphenol glycoside of the present invention has been found to have glucosidase inhibitory activity several times stronger than that of isoquercitrin. In addition, the polyphenol glycoside of the present invention has been found to have glucosidase inhibitory activity several times stronger than that of taxifolin, which has a structure analogous to that of the polyphenol glycoside of the present invention. It is predicted that high glucosidase inhibitory activity of the glycoside of the present invention is caused by the aforementioned characteristic binding mode.

The polyphenol glycoside of the present invention can be prepared through purification and isolation from an acerola fruit or a processed product thereof.

The area of production or the variety of acerola is not particularly limited. For example, acerola can be produced in Okinawa, Japan, or in Brazil. The term "fruit" used herein refers to the whole fruit, including edible parts and seeds.

Examples of a processed product of an acerola fruit used herein include, but are not limited to, acerola juice obtained by squeezing an acerola fruit by a conventional method, concentrated acerola juice obtained by concentrating acerola juice, a product obtained by allowing concentrated acerola juice to be subjected to yeast fermentation and removing glucose and fructose from the resultant, and a product of crushed acerola obtained by, for example, crushing and grinding an acerola fruit (edible parts and seeds or edible parts from which seeds have been removed) by a mixer or the like. These examples may be further dehydrated via a conventional method involving air drying, drying under reduced pressure, lyophilization, spray drying, or other means to form powders. In such a case, the processed product may be mixed with an excipient (e.g., dietary fiber or calcium oxide) or the like for dehydration.

An isolation method is not particularly limited. However, preferably, an acerola fruit or a processed product thereof is subjected to liquid-liquid fractionation with the use of a solvent system of water/ethyl acetate so that an aqueous layer fraction is recovered. Then, the obtained aqueous layer fraction is subjected to liquid-liquid fractionation with the use of a solvent system of water/butanol so that a butanol layer fraction is recovered. Thereafter, the obtained butanol layer fraction is subjected to isolation and purification by a conventional method. Thus, the polyphenol glycoside of the present invention is obtained. According to the above method, an aqueous layer fraction is recovered in a step after liquid-liquid fractionation with the use of a water/ethyl acetate system so as to be subjected to liquid-liquid fractionation with the use of a water/butanol system. Thus, the method significantly differs from a conventional method for isolating and purifying polyphenols, in which an ethyl acetate fraction is recovered in a step after liquid-liquid fractionation with the use of a water/ethyl acetate system.

Purification treatment may be carried out via, for example, normal-phase or reverse-phase chromatography, chromatography with the use of a synthetic adsorbent, ion-exchange chromatography, or gel filtration. These techniques may be carried out in combination.

The polyphenol glycoside of the present invention that serves as an antioxidant or glucosidase inhibitor is not necessarily isolated as a pure compound and thus it may be provided in the form of a mixture with other components isolated from acerola. For instance, the polyphenol glycoside of the present invention may be provided in the form of a mixture with acerola-polyphenols (e.g., anthocyanin pigments such as cyanidin-3-rhamnoside and pelargonidin-3-rhamnoside; quercetin glycosides such as quercitrin (quercetin-3-rhamnoside), isoquercitrin (quercetin-3-glucoside), and hyperoside (quercetin-3-galactoside); and astilbin).

The polyphenol glycoside of the present invention may be formulated in combination with known carriers for medical use. Such a pharmaceutical preparation can be administered as an antioxidant or glucosidase inhibitor.

Dosage form is not particularly limited, and it is adequately determined according to need. In general, dosage forms can be: oral preparations such as tablets, capsules, granules, fine granules, powders, pills, liquids, syrups, suspensions, emulsions, and elixirs; or parenteral preparations such as injections, drops, suppositories, inhalants, transmucosal absorbents, transnasal preparations, enteral preparations, and skin preparations for external use (e.g., transdermal absorbents, adhesive preparations, and ointments). These preparations are used alone or in combinations of two or more in accordance with symptoms. Preferably, the polyphenol glycoside of the present invention, which serves as a glucosidase inhibitor, is in the form of an oral agent. Also, the polyphenol glycoside of the present invention, which serves as an antioxidant, is preferably in the form of an oral agent or skin preparation for external use.

The dose of a pharmaceutical preparation of the polyphenol glycoside of the present invention varies depending on the age and the body weight of the patient, the severity of disease, and the route of administration. In the case of oral administration, the amount of the polyphenol glycoside of the present invention is usually 0.1 mg to 1,000 mg per day.

The aforementioned pharmaceutical preparation can be prepared by conventional methods with the use of excipients, binders, disintegrators, surfactants, lubricants, flow promoters, taste corrigents, colorants, fragrant materials, and the like.

Specific examples of excipients include starch, lactose, sucrose, mannite, carboxymethylcellulose, cornstarch, and an inorganic salt.

Specific examples of binders include crystalline cellulose, crystalline cellulose carmellose sodium, methylcellulose, hydroxypropylcellulose, low-substituted hydroxypropylcellulose, hydroxypropylmethylcellulose, hydroxypropylmethylcellulose phthalate, hydroxypropylmethylcellulose acetate succinate, carmellose sodium, ethyl cellulose, carboxy methyl ethyl cellulose, hydroxyethyl cellulose, wheat starch, rice starch, cornstarch, potato starch, dextrin, pregelatinized starch, partially pregelatinized starch, hydroxypropyl starch, Pullulan, polyvinylpyrrolidone, aminoalkyl methacrylate copolymer E, aminoalkyl methacrylate copolymer RS, mechacrylic acid copolymer L, mechacrylic acid copolymer, polyvinylacetal diethylaminoacetate, polyvinyl alcohol, gum Arabic, powdered acacia, agar, gelatin, white shellac, tragacanth, purified sucrose, and Macrogol.

Specific examples of disintegrators include crystalline cellulose, methylcellulose, low-substituted hydroxypropylcellulose, carmellose, carmellose calcium, carmellose sodium, croscarmellose sodium, wheat starch, rice starch, cornstarch, potato starch, partially pregelatinized starch, hydroxypropyl starch, sodium carboxymethyl starch, and tragacanth.

Specific examples of surfactants include soybean lecithin, sucrose fatty acid ester, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, and lauromacrogol.

Specific examples of lubricants include wheat starch, rice starch, cornstarch, stearic acid, calcium stearate, magnesium stearate, hydrated silicon dioxide, light anhydrous silicic acid, synthetic aluminum silicate, dried aluminum hydroxide gel, talc, magnesium aluminometasilicate, calcium hydrogen phosphate, anhydrous dibasic calcium phosphate, sucrose fatty acid ester, waxes, hydrogenated vegetable oil, and polyethylene glycol.

Specific examples of flow promoters include hydrated silicon dioxide, light anhydrous silicic acid, dried aluminum hydroxide gel, synthetic aluminum silicate, and magnesium silicate.

In addition, upon administration of the aforementioned pharmaceutical preparation in the form of a liquid, syrup, suspension, emulsion, or elixir, it may contain a taste and flavor corrigent or a colorant.

The polyphenol glycoside of the present invention can be added to solid, semisolid, or liquid food products, or to food products in other forms, in accordance with conventional techniques. Such food can be ingested as a food having antioxidative activity or glucosidase inhibitory activity. Examples of solid food products include, but are not limited to, block-shaped confectioneries such as biscuits and powdery food products such as powdered soup. Also, a processed product of an acerola fruit containing the polyphenol glycoside of the present invention at a high concentration can also be used as a food product in such state. Examples of semisolid food products include capsules and jellies. Examples of beverages include fruit juice beverages, soft drink beverages, and alcoholic beverages. Alternatively, a beverage may be in the form of powder that is diluted with a liquid carrier such as water before ingestion. Further, such foods containing the polyphenol glycoside of the present invention can be prepared as so-called foods for specified health uses.

According to need, a stabilizer, a pH adjuster, saccharides, a sweetener, various vitamins, minerals, an antioxidant, an excipient, a solubilizer, a binder, a lubricant, a suspension, a moistening agent, a film-forming substance, a taste corrigent, a flavor corrigent, a colorant, a fragrant material, a preservative, and the like can be added to the aforementioned food products in accordance with conventional techniques.

The polyphenol glycoside of the present invention may be added to various types of cosmetics in accordance with conventional techniques. Examples of such cosmetics include: basic skin care cosmetics such as lotions, emulsions, creams, and facial masks; cosmetics for makeup such as foundations and lipsticks; and medical cosmetics. Such cosmetics may have, for example, effects based on antioxidative activity (e.g., skin-whitening effects) and effects based on glucosidase inhibitory activity of the polyphenol glycoside.

Hitherto, acerola, which is the starting material for production of the pharmaceutical preparation of the present invention, has been applied to pharmaceutical preparations, foods, beverages, cosmetics, and the like. The safety of acerola has been established.

EXAMPLE 1

Acerola powders (Nichirei Corporation, Nichirei acerola powder VC 30) were used as the starting material for preparing a polyphenol glycoside that is a product of the present invention. The powders are obtained by allowing concentrated acerola juice to be subjected to yeast fermentation, removing glucose and fructose from the resultant, and dissolving excipients such as dietary fiber and calcium oxide therein, followed by powderization.

400 g of the thus obtained acerola powders were dissolved in purified water for preparing 2,000 g of a 20% (W/W) aqueous solution. Ethyl acetate in a volume (cubic volume basis) equivalent to half of that of the resulting aqueous solution was added to the aqueous solution, followed by agitation. Then, liquid-liquid fractionation was carried out with the use of a separatory funnel such that an aqueous layer fraction was recovered. Butanol in a volume (cubic volume basis) equivalent to half of that of the resulting aqueous layer fraction was added to the obtained fraction, followed by agitation. Then, liquid-liquid fractionation was carried out with the use of a separatory funnel such that a butanol layer fraction was recovered. Purified water in an adequate volume was added to the obtained butanol layer fraction, followed by vacuum distillation treatment for dehydration. Accordingly, 24 g of solid matter was recovered.

The above solid matter was dissolved in 50 mL of purified water, followed by partial purification with the use of a C18 column (Sep-Pak Vac 35 cc (10 g) C18 cartridges, Waters). During such purification, the obtained sample was loaded into the column, followed by column washing with purified water and a 10% methanol aqueous solution. Thereafter, a fraction was eluted with a 20% methanol aqueous solution so as to be recovered. The obtained fraction was evaporated to dryness by a vacuum distiller. Accordingly, 0.8 g of solid matter was recovered.

The above solid matter was dissolved in 10 ml of a 20% methanol aqueous solution. The obtained sample was subjected to high-purity purification by high performance liquid chromatography. The column used for preparative isolation was Inertsil ODS-3 (5 μm, 4.6×250 mm (GL-science)). During the preparative isolation operation, the sample (0.5 ml each for a single operation) was loaded into the column, the column was washed with a 10% methanol aqueous solution, elution was performed with a methanol concentration gradient of 10% to 50%, and peaks containing the target polyphenol glycoside were fractionated. Such preparative isolation operation was repeated 20 times.

The methanol aqueous solution comprising the polyphenol glycoside of the present invention that had been purified by the above method was dehydrated using a vacuum distiller. The resultant was suspended in purified water. Then, insoluble matter thereof was separated from the supernatant by centrifugation so as to be recovered. The obtained insoluble matter was again dissolved in methanol and evaporated to dryness using a vacuum distiller. The resultant was suspended again in purified water. Then, the resulting insoluble matter was recovered. After recovery of the insoluble matter, the moisture content thereof was removed by a lyophilizer. Accordingly, 10 mg of the polyphenol glycoside of the present invention was obtained.

It was also possible to recover the product of the present invention from acerola concentrated juice by procedures and methods similar to those described above. However, the purity of the product recovered from the acerola powders was higher than that recovered from acerola concentrated juice.

EXAMPLE 2

The structure of polyphenol glycoside of the present invention which had been isolated in Example 1 was determined by various forms of spectrum measurement.

Table 1 shows measurement conditions.

TABLE 1

| Measurement conditions | |
|---|---|
| High-resolution ESI-MS | |
| Apparatus: | LCT mass spectrometer (Micromass) |
| Mobile phase: | Methanol (0.1 mL/min) |
| Volume of sample solution injected: | 5 μl |
| Ions to be measured: | Positive ions |
| Sample introduction: | Pulse injection |
| Spraying voltage: | 3,000 V |
| Cone voltage: | 30 V |
| Ext. cone voltage: | 2 V |
| Desolvation unit temperature: | 150° C. |
| Ion source temperature: | 120° C. |

TABLE 1-continued

Measurement conditions

| | |
|---|---|
| RF Lens: | 200 units |
| Desolvation gas: | Nitrogen (approximately 700 L/hr) |
| Scan range: | m/z 150 to 1,000 (1 sec) |
| Scan interval: | 0.1 sec |
| Internal standard substance: | Leucine enkephalin |
| NMR | |
| Apparatus: | UNITY INOVA 500 (Varian) |
| Observation frequency: | $^1$H: 499.8 MHz, $^{13}$C: 125.7 MHz |
| Solvent: | CD$_3$OD |
| Concentration: | 6.3 mg/0.65 mL |
| Standard: | TMS |
| Temperature: | 25° C. |
| $^1$H NMR measurement: | |
| Observation width: | 5 KHz |
| Data point: | 64K |
| Pulse angle: | 30° |
| Pulse repetition time: | 10 sec |
| Repetitions: | 16 times |
| $^{13}$C NMR measurement: | |
| Observation width: | 30 KHz |
| Data point: | 64K |
| Pulse angle: | 45° |
| Pulse repetition time: | 3 sec |
| Repetitions: | 2,400 times |
| DEPT measurement: (measurement of CH and CH$_3$ with positive signals and of CH$_2$ with negative signals) | |
| Observation width: | 30 KHz |
| Data point: | 64K |
| Pulse repetition time: | 3 sec |
| Repetitions: | 800 times |
| DQF-COSY measurement: | |
| Observation width: | t2 axis: 5 KHz |
| | t1 axis: 5 KHz |
| Data point: | t2 axis: 2048 |
| | t1 axis: 256 × 2 (zero filling to 2048) |
| Pulse waiting time: | 3 sec |
| Repetitions: | 16 times |
| HSQC measurement | |
| Observation width: | t2 axis: 20 KHz |
| | t1 axis: 5 KHz |
| Data point: | t2 axis: 2048 |
| | t1 axis: 256 × 2 (zero filling to 2048) |
| Pulse waiting time: | 2.5 sec |
| Repetitions: | 16 times |
| HMBC measurement: | |
| Observation width: | t2 axis: 25 KHz |
| | t1 axis: 5 KHz |
| Data point: | t2 axis: 2048 |
| | t1 axis: 512 (zero filling to 2048) |
| Pulse waiting time: | 2.5 sec |
| Repetitions: | 32 times |
| NOESY measurement: | |
| Observation width: | t2 axis: 5 KHz |
| | t1 axis: 5 KHz |
| Data point: | t2 axis: 2048 |
| | t1 axis: 256 × 2 (zero filling to 2048) |
| Mixing time: | 1 sec |
| Pulse waiting time: | 3.446 sec |
| Repetitions: | 16 times |

Abbreviations
DEPT: Distortionless Enhancement by Polarization Transfer (A method for determining a carbon type (distinguishing among CH$_3$, CH$_2$, CH, and C))
DQF-COSY: Double Quantum Filtered COrrelation SpectroscopY (A method of $^1$H-$^1$H COSY)
NOESY: Nuclear Overhauser Effect SpectroscopY
HSQC: Heteronuclear Single Quantum Coherence (A method of $^1$H-$^{13}$C COSY)
HMBC: Heteronuclear Multiple Bond Correlation (A method of long-range $^1$H-$^{13}$C COSY)

High Resolution ESI-MS

Figure 1A:
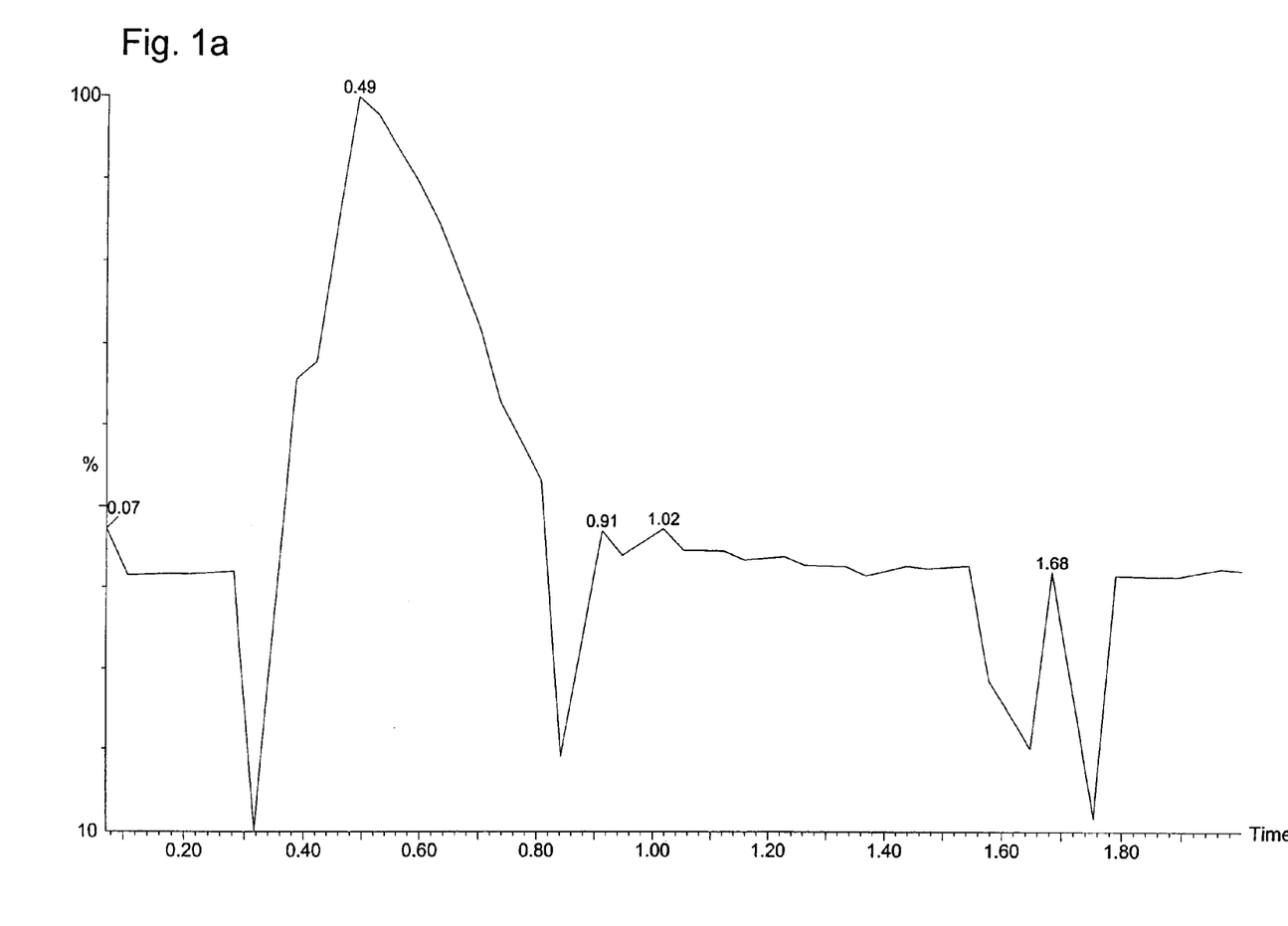
FIG. 1a shows a total ion chromatogram of the compound of the present invention.
Figure 1B:
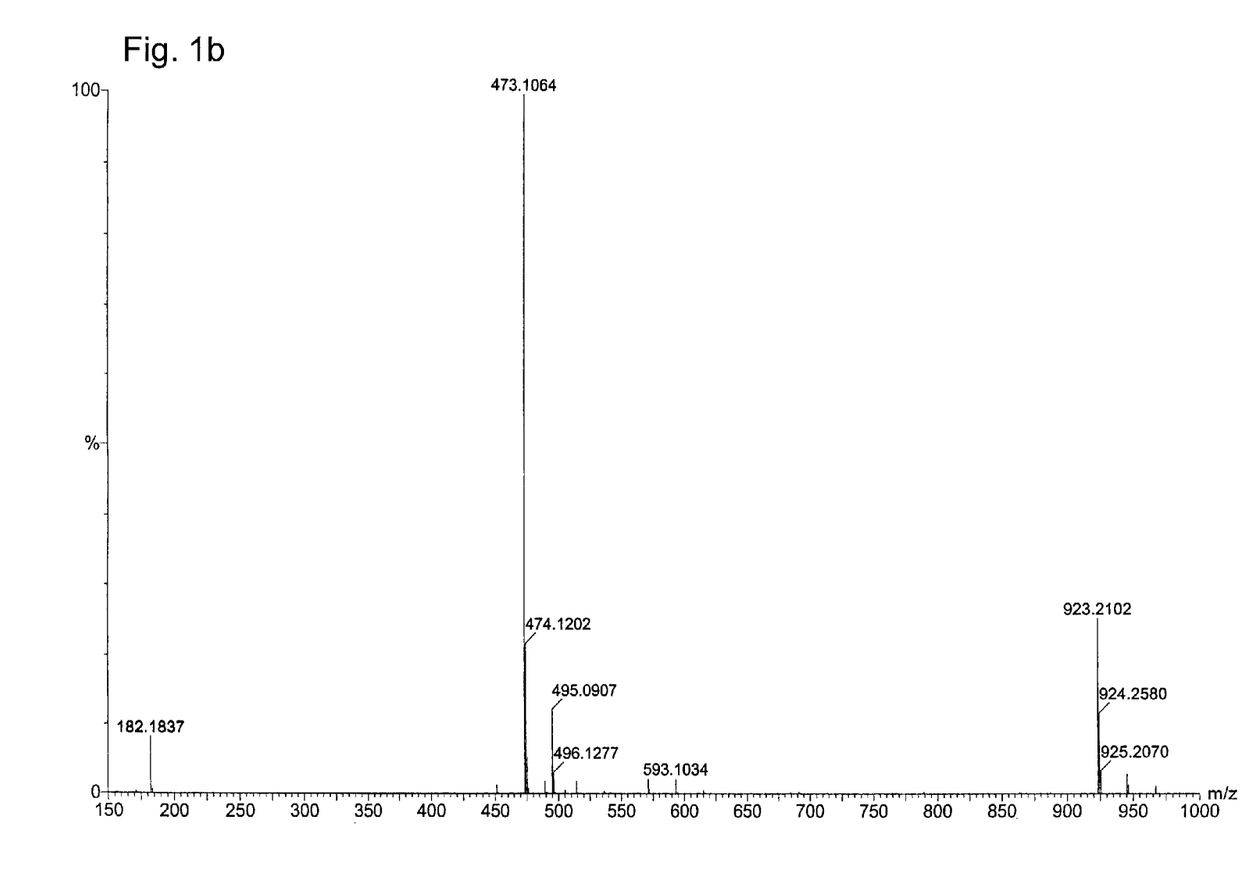
FIG. 1b shows high resolution ESI mass spectra of the compound of the present invention.

FIG. 1a shows a total ion chromatogram. FIG. 1b shows a high resolution ESI mass spectrum. Upon this measurement, an m/z 473 sodium adduct ion (M+Na)$^+$ was strongly observed. Composition calculation was performed with the use of the accurate mass (found value) of the ion (m/z 473.1064). Upon composition calculation, elements of C, H, O, and Na were used. The resulting composition formula was determined to be $C_{21}H_{22}O_{11}Na$. A theoretical value of the accurate mass of the ion was m/z 473.1060. An error between the found value and the theoretical value was 0.4 mDa. Thus, considering that the sodium adduct ion was measured in this measurement, the composition formula of the compound of the present invention is $C_{21}H_{22}O_{11}$ and the molecular weight thereof is 450.

NMR Measurement

The analysis was carried forward with the use of alphabetical symbols "a" to "o" for $^1$H NMR signals and alphabetical symbols "A" to "U" for $^{13}$C NMR signals depending on magnetic field levels in descending order (starting from the rightmost signal).

$^1$H NMR

Figure 2:
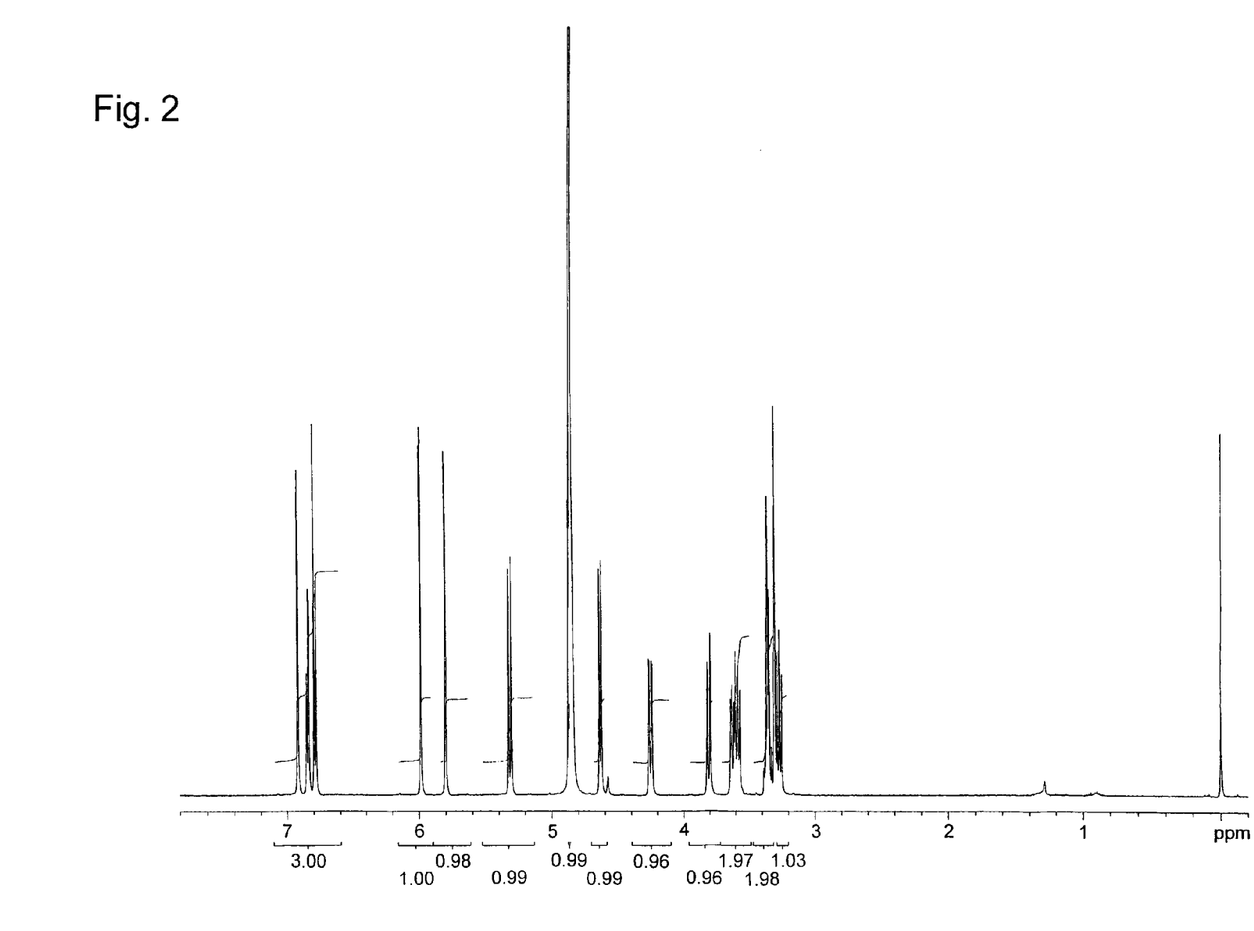
FIG. 2 shows $^1$H NMR spectra of the compound of the present invention.

FIG. 2 shows $^1$H NMR spectra. Table 2 shows a list of signals.

TABLE 2

| FREQUENCY(PPM) | Hz | SUB | HEIGHT |
|---|---|---|---|
| 6.920 | 3458.710 | −3458.710 | 404.1 |
| 6.916 | 3456.879 | 1.831 | 434.4 |
| 6.854 | 3425.903 | 30.975 | 161.4 |
| 6.850 | 3423.920 | 1.984 | 147.3 |
| 6.838 | 3417.816 | 6.104 | 274.7 |
| 6.834 | 3415.833 | 1.984 | 259.7 |
| 6.795 | 3396.454 | 19.379 | 495.8 |
| 6.779 | 3388.367 | 8.087 | 295.5 |
| 5.987 | 2992.706 | 395.660 | 467.1 |
| 5.983 | 2990.417 | 2.289 | 491.9 |
| 5.802 | 2899.933 | 90.485 | 459.7 |
| 5.797 | 2897.644 | 2.289 | 442.6 |
| 5.325 | 2661.896 | 235.748 | 301.3 |
| 5.303 | 2650.909 | 10.986 | 317.5 |
| 4.872 | 2435.150 | 215.759 | 393.5 |
| 4.865 | 2431.793 | 3.357 | 494.3 |
| 4.850 | 2424.164 | 7.629 | 8167.5 |
| 4.640 | 2319.336 | 104.828 | 301.6 |
| 4.624 | 2311.401 | 7.935 | 312.7 |
| 4.577 | 2287.750 | 23.651 | 23.6 |
| 4.267 | 2133.026 | 154.724 | 180.7 |
| 4.261 | 2129.669 | 3.357 | 178.2 |
| 4.245 | 2122.040 | 7.629 | 177.6 |
| 4.239 | 2118.683 | 3.357 | 173.1 |
| 3.819 | 1909.027 | 209.656 | 175.8 |
| 3.797 | 1897.888 | 11.139 | 213.7 |
| 3.794 | 1896.515 | 1.373 | 206.9 |
| 3.638 | 1818.390 | 78.125 | 125.0 |
| 3.628 | 1813.354 | 5.035 | 144.5 |
| 3.614 | 1806.335 | 7.019 | 121.1 |
| 3.603 | 1800.690 | 5.646 | 190.3 |
| 3.585 | 1791.840 | 8.850 | 162.1 |
| 3.583 | 1790.924 | 0.916 | 161.4 |
| 3.566 | 1782.532 | 8.392 | 137.3 |
| 3.387 | 1692.963 | 89.569 | 34.9 |
| 3.361 | 1679.840 | 13.123 | 398.1 |
| 3.348 | 1673.431 | 6.409 | 273.7 |
| 3.328 | 1663.666 | 9.766 | 61.3 |
| 3.309 | 1653.748 | 9.918 | 385.3 |
| 3.305 | 1652.222 | 1.526 | 520.1 |
| 3.302 | 1650.696 | 1.526 | 398.0 |
| 3.299 | 1649.170 | 1.526 | 228.9 |
| 3.285 | 1642.151 | 7.019 | 189.1 |
| 3.269 | 1634.064 | 8.087 | 218.5 |
| 3.266 | 1632.538 | 1.526 | 206.6 |
| 3.250 | 1624.603 | 7.935 | 158.9 |

TABLE 2-continued

| FREQUENCY(PPM) | Hz | SUB | HEIGHT |
|---|---|---|---|
| 1.286 | 642.548 | 982.056 | 18.9 |
| 0.000 | 0.000 | 642.548 | 484.1 |

Based on $^1$H NMR spectra, the existence of partial configurations of 1,2,4-trisubstituted benzene ("o," "n," or "m" signal) and 1,2,4,5-tetrasubstituted benzene ("l" or "k" signal) were confirmed. In addition, signals "a" to "j" were determined to be attributed to $CH_n$—O (n=1 or 2) based on chemical shift values.

$^3$C NMR

Figure 3:
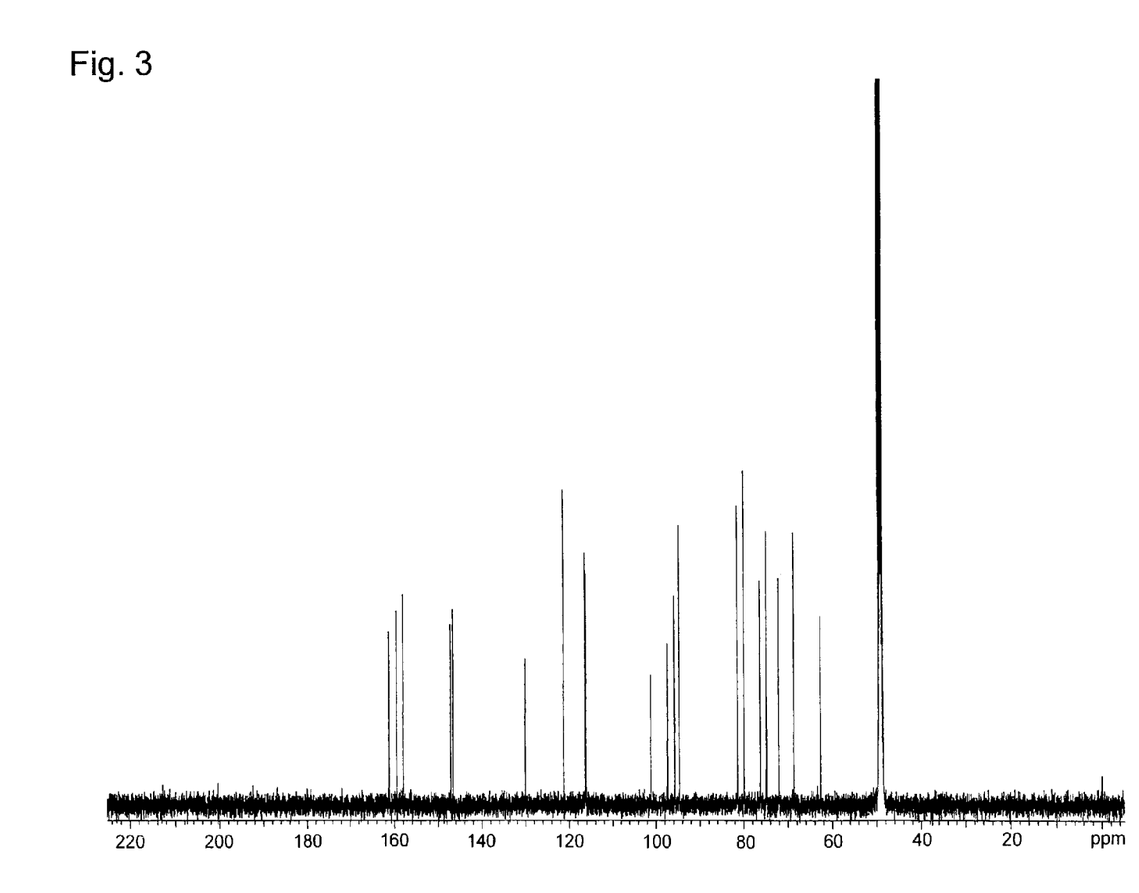
FIG. 3 shows $^{13}$C NMR spectra of the compound of the present invention.

FIG. 3 shows $^{13}$C NMR spectra. Table 3 shows a list of signals.

TABLE 3

| FREQUENCY(PPM) | Hz | SUB | HEIGHT |
|---|---|---|---|
| 161.130 | 20251.680 | −20251.680 | 58.1 |
| 159.397 | 20033.812 | 217.868 | 65.1 |
| 157.918 | 19847.983 | 185.829 | 70.4 |
| 147.073 | 18484.933 | 1363.050 | 60.6 |
| 146.527 | 18416.277 | 68.656 | 65.7 |
| 130.016 | 16341.036 | 2075.241 | 49.2 |
| 121.217 | 15235.217 | 1105.819 | 106.0 |
| 116.294 | 14616.398 | 618.819 | 84.4 |
| 116.090 | 14590.766 | 25.632 | 77.5 |
| 101.115 | 12708.678 | 1882.089 | 43.7 |
| 97.313 | 12230.832 | 477.846 | 54.0 |
| 95.733 | 12032.187 | 198.645 | 70.1 |
| 94.626 | 11893.045 | 139.143 | 93.7 |
| 81.355 | 10225.162 | 1667.882 | 100.6 |
| 79.899 | 10042.080 | 183.083 | 112.6 |
| 76.257 | 9584.373 | 457.706 | 74.9 |

TABLE 3-continued

| FREQUENCY(PPM) | Hz | SUB | HEIGHT |
|---|---|---|---|
| 74.866 | 9409.529 | 174.844 | 88.3 |
| 74.808 | 9402.206 | 7.323 | 91.8 |
| 72.055 | 9056.180 | 346.026 | 75.9 |
| 68.639 | 8626.851 | 429.329 | 91.2 |
| 62.608 | 7868.889 | 757.962 | 63.1 |
| 49.563 | 6229.385 | 1639.505 | 761.5 |
| 49.396 | 6208.330 | 21.054 | 2610.4 |
| 49.228 | 6187.276 | 21.054 | 4509.3 |
| 49.054 | 6165.306 | 21.970 | 5972.0 |
| 48.886 | 6144.251 | 21.054 | 5092.5 |
| 48.711 | 6122.282 | 21.970 | 2329.7 |
| 48.544 | 6101.227 | 21.054 | 898.4 |
| 0.000 | 0.000 | 6101.227 | 9.8 |

Based on $^{13}$C NMR spectra, 21 signals were observed. The results were consistent with those obtained upon MS measurement. The signal of ketonecarbonyl was not observed.

DEPT

Figure 4:
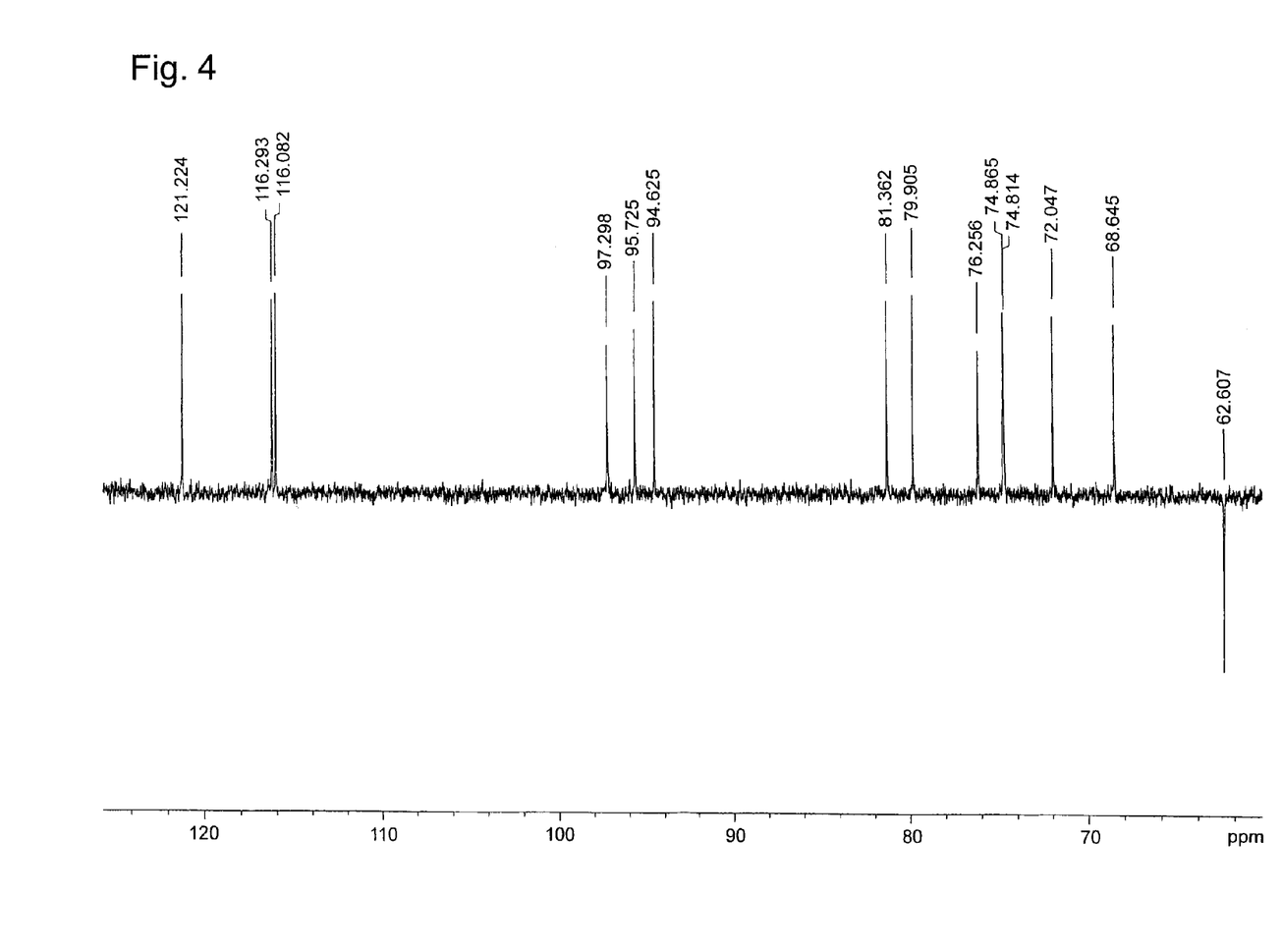
FIG. 4 shows DEPT spectra of the compound of the present invention.

FIG. 4 shows DEPT spectra. Based on the spectra, carbons to which the signals were attributed were determined (see table 4).

DQF-COSY

Figure 5:
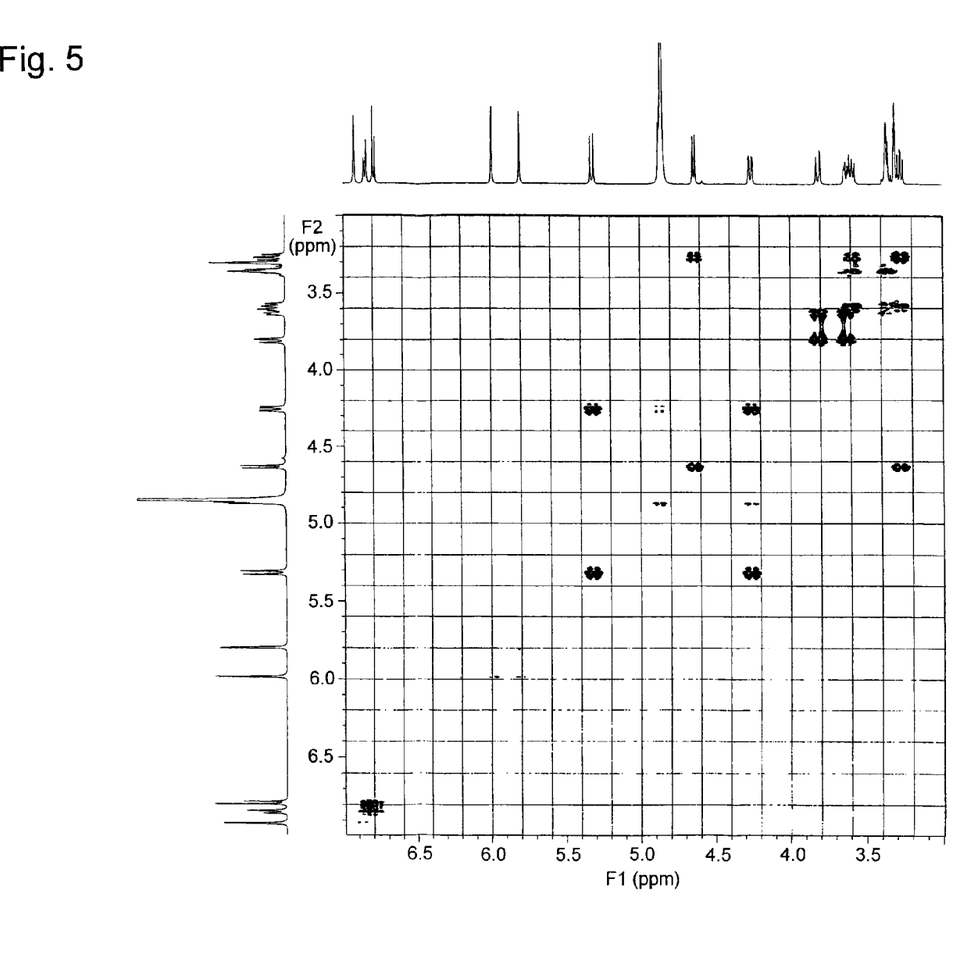
FIG. 5 shows DQF-COSY spectra of the compound of the present invention.

FIG. 5 shows DQF-COSY spectra. Based on the spectra, the following partial structures were obtained.

(1) j (5.31 ppm)-g (4.25 ppm)-I (4.87 ppm) —CH(j)-CH(g)-CH(i)-

(2) h (4.63 ppm)-a(3.27 ppm)-d(3.58 ppm)-b(3.35 ppm) or c
f(3.81 ppm)-e(3.62 ppm)-c(3.36 ppm) or b

HSQC

Figure 6:
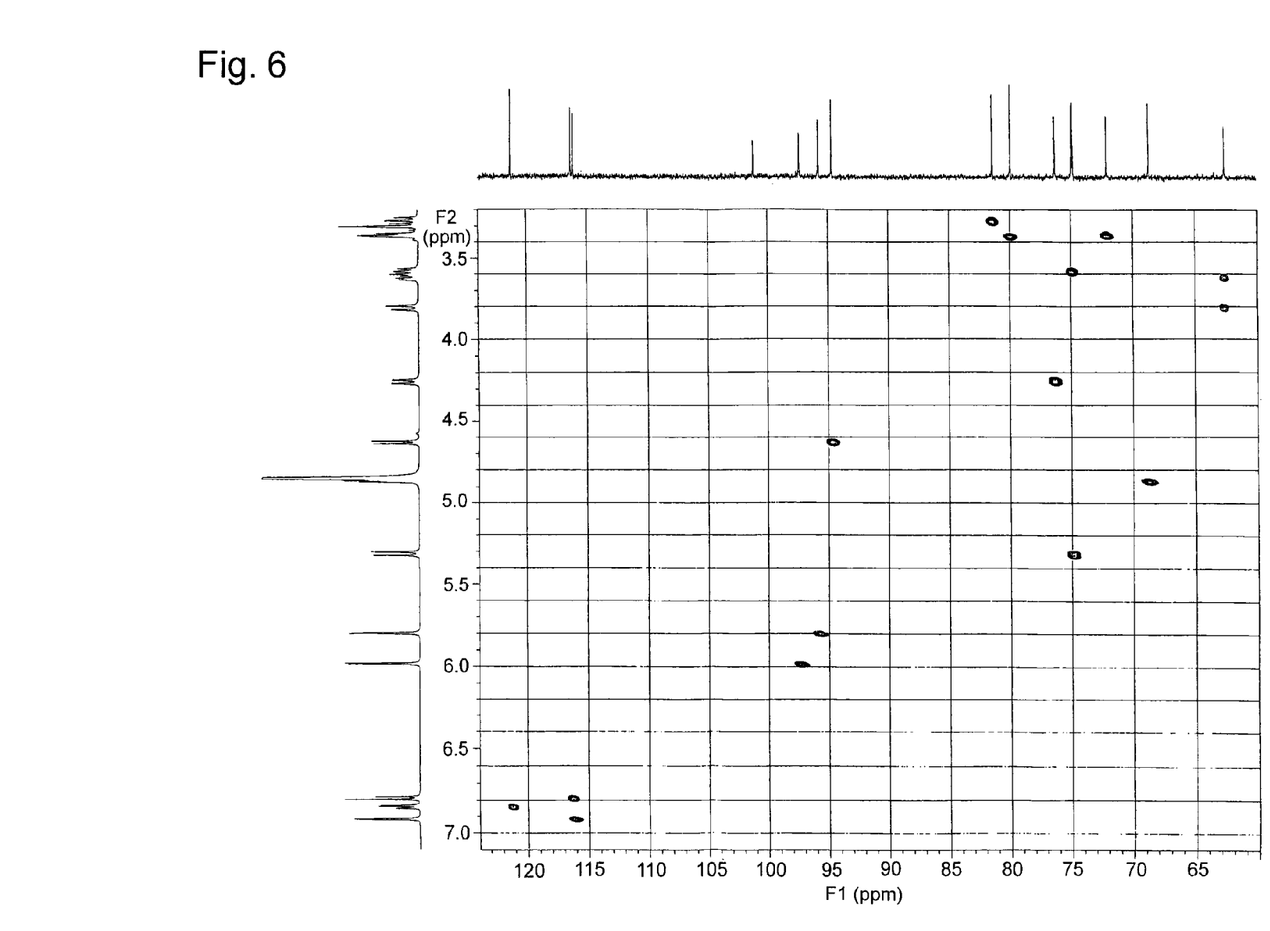
FIG. 6 shows HSQC spectra of the compound of the present invention.

FIG. 6 shows HSQC spectra. Based on HSQC spectra, $^1$H and $^{13}$C, which bind to each other at $^1$J($^1$H, $^{13}$C), were determined. The results are summarized in table 4.

TABLE 4

Types of $^{13}$C, chemical shifts of $^{13}$C, Chemical shifts of $^1$H to be bound to $^{13}$C, and spin coupling constants

| $^{13}$C signal | Type of $^{13}$C | Chemical shift of $^{13}$C (ppm) | Chemical shift of $^1$H to be bound $^{13}$C (ppm) | Spin coupling constant J(Hz) |
|---|---|---|---|---|
| A | $CH_2$ | 62.6 | e(3.62), f(3.81) | $J_{e,f}$ = 12.1, $J_{e,c}$ = 5.3, $J_{f,c}$ = 1.4 |
| B | CH | 68.6 | i(4.87) | $J_{i,g}$ = 3.4 |
| C | CH | 72.1 | b(3.35) | |
| D | CH | 74.8 | j(5.31) | $J_{j,g}$ = 11.0 |
| E | CH | 74.9 | d(3.58) | $J_{d,b}$ = 8.4 |
| F | CH | 76.3 | g(4.25) | |
| G | CH | 79.9 | c(3.36) | |
| H | CH | 81.4 | a(3.27) | $J_{a,d}$ = 9.5 |
| I | CH | 94.6 | h(4.63) | $J_{a,h}$ = 7.9 |
| J | CH | 95.7 | k(5.80) | $J_{k,l}$ = 2.3 |
| K | CH | 97.3 | l(5.99) | |
| L | C | 101.1 | — | — |
| M | CH | 116.1 | o(6.92) | $J_{o,n}$ = 2.0 |
| N | CH | 116.3 | m(6.79) | $J_{m,n}$ = 8.1 |
| O | CH | 121.2 | n(6.84) | |
| P | C | 130.0 | — | — |
| Q | C | 146.5 | — | — |
| R | C | 147.1 | — | — |
| S | C | 157.9 | — | — |

TABLE 4-continued

| $^{13}C$ signal | Type of $^{13}C$ | Chemical shift of $^{13}C$ (ppm) | Chemical shift of $^{1}H$ to be bound $^{13}C$ (ppm) | Spin coupling constant J(Hz) |
|---|---|---|---|---|
| T | C | 159.4 | — | — |
| U | C | 161.1 | — | — |

HMBC

Figure 7:
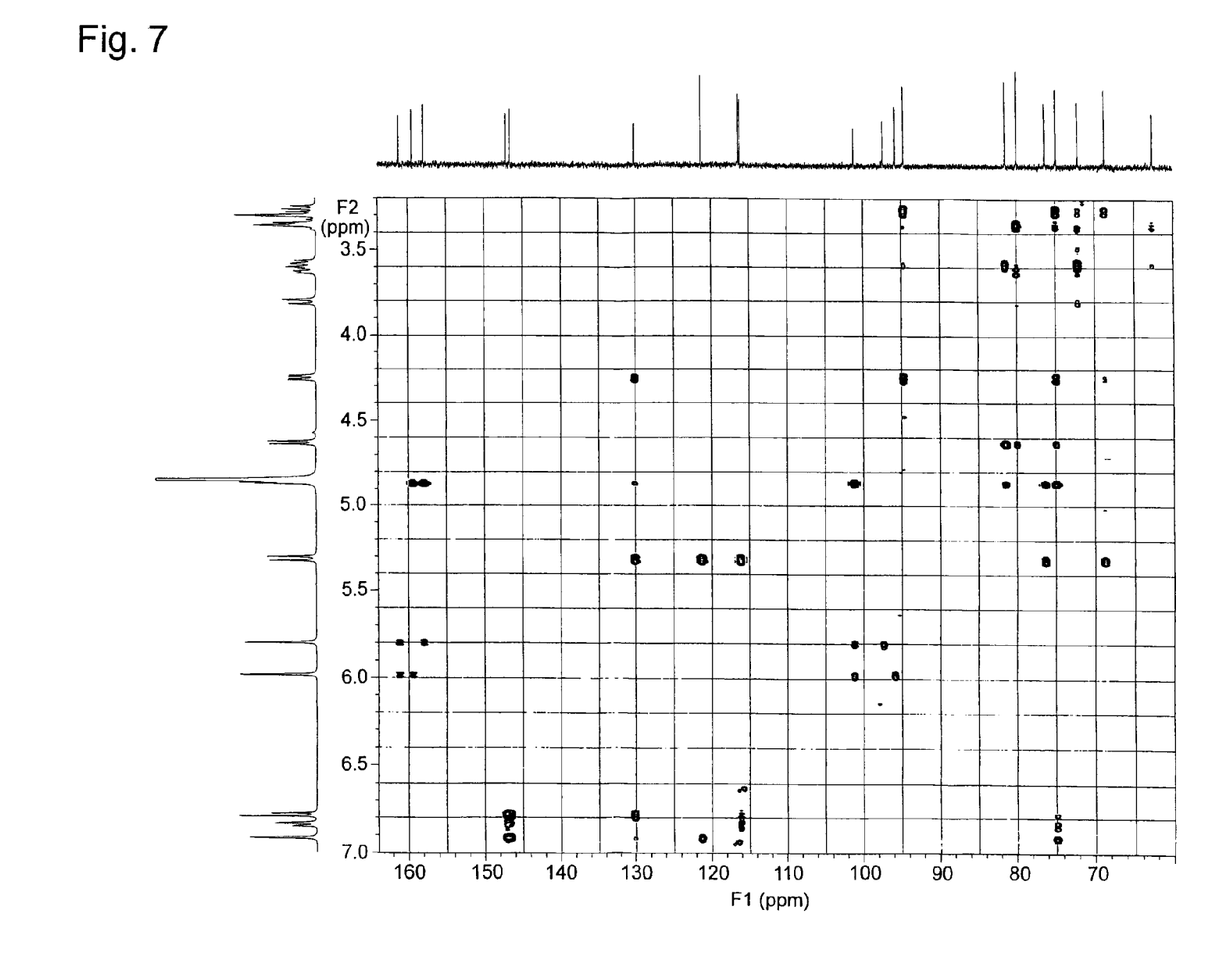
FIG. 7 shows HMBC spectra of the compound of the present invention.

FIG. 7 shows HMBC spectra. Table 5 lists representative long-range correlation signals observed in HMBC spectra.

TABLE 5 a - B, C, E, I
b - A, E, G
c - C, E
d - C, H, I
e, f - C, G
g - B, D, I, P
h - E, G, H
i - D, F, H, L, S, T
j - B, F, M, O, P, S
k - K, L, S, U
l - J, L, T, U
m - P, Q, R
n - D, M, R
o - D, O, R

Based on the above results, the 2-dimensional structure of the compound of the present invention was obtained.

NOESY Measurement

Figure 8:
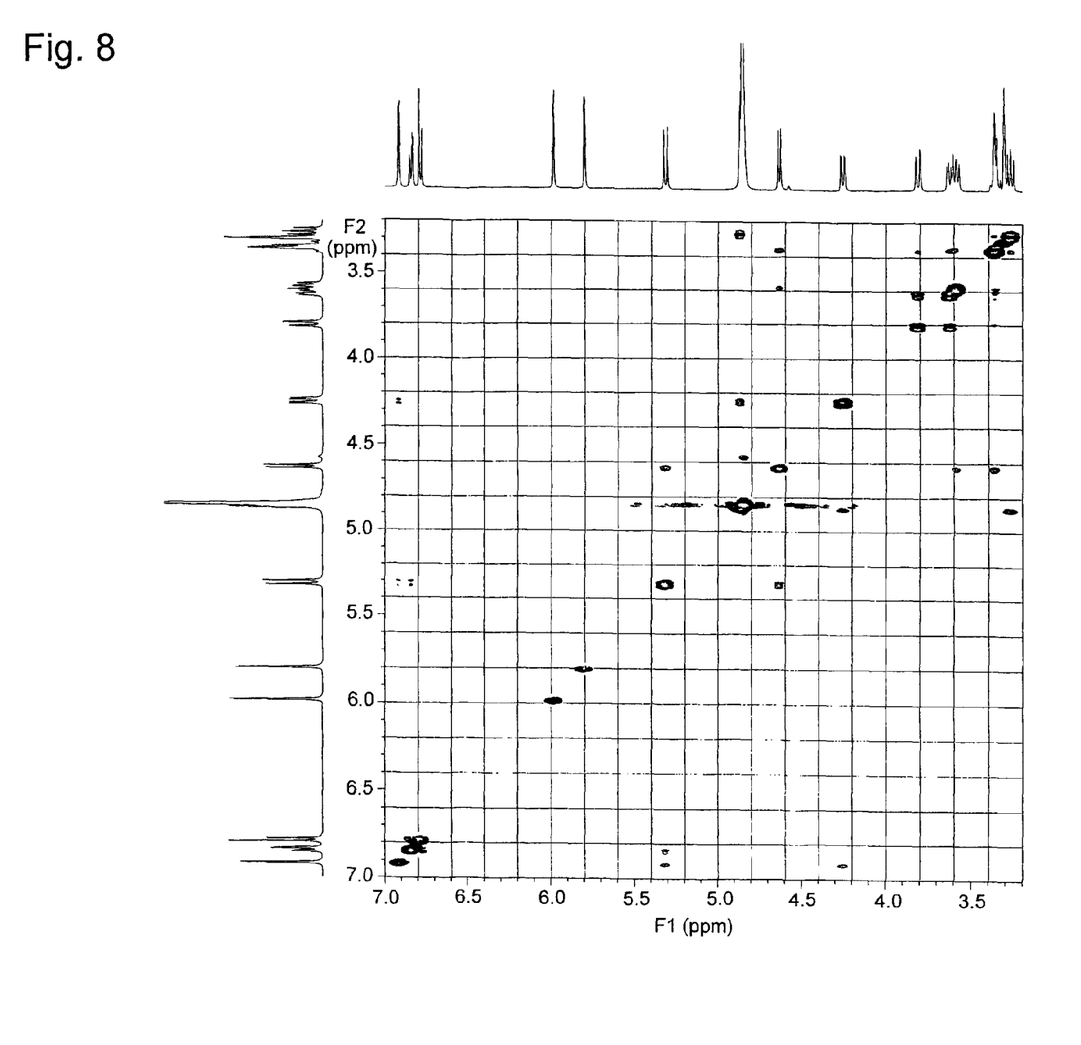
FIG. 8 shows NOESY spectra of the compound of the present invention.

FIG. 8 shows NOESY spectra. Based on NOESY spectra, the following inter-proton correlation signals were observed.

Spin coupling constants of $J_{h,a}$=7.9 Hz, $J_{a,d}$=9.5 Hz and $J_{d,b}$=8.4 Hz which are characteristic to sugars indicated the axial-axial form.

An NOE was observed between protons "h" and "c." Thus, proton "c" was confirmed to be at an axial position. Therefore, the sugar component of the compound of the present invention was determined as β-glucose.

Based on HMBC correlation signals between proton "g" and carbon "I," between proton "i" and carbon "H," and between proton "a" and carbon "B," the glucose was considered to have a structure in which OH at position 1 and OH at position 2 respectively form bonds as described above.

Based on NOEs between "A" and "i," between "h" and "j," and between "g" and "i," the relative configuration of protons "j," "g," and "i" was predicted as described above.

The constants of $J_{i,g}$=11.0 Hz and $J_{g,i}$=3.4 Hz correspond to the above relative configuration.

Table 6 is an assignment table in which numbered atoms are listed.

TABLE 6

NMR assignment table

| Carbon number | Chemical shift of $^{13}C$ (ppm) | Chemical shift of $^{1}H$ (ppm) | Spin coupling constant J(Hz) |
|---|---|---|---|
| 2 | 74.8 | 5.31 | $J_{2,3}$ = 11.0 |
| 3 | 76.3 | 4.25 | $J_{3,4}$ = 3.4 |
| 4 | 68.6 | 4.87 | |
| 4a | 101.1 | — | — |
| 5 | 159.4 | — | — |
| 6 | 97.3 | 5.99 | $J_{6,8}$ = 2.3 |
| 7 | 161.1 | — | — |
| 8 | 95.7 | 5.80 | $J_{6,8}$ = 2.3 |
| 8a | 157.9 | — | — |
| 1' | 130.0 | — | — |
| 2' | 116.1 | 6.92 | $J_{2',6'}$ = 2.0 |
| 3' | 146.5 | — | — |
| 4' | 147.1 | — | — |
| 5' | 116.3 | 6.79 | $J_{5',6'}$ = 8.1 |
| 6' | 121.2 | 6.84 | |
| 1" | 94.6 | 4.63 | $J_{1",2"}$ = 7.9 |
| 2" | 81.4 | 3.27 | $J_{2",3"}$ = 9.5 |
| 3" | 74.9 | 3.58 | $J_{3",4"}$ = 8.4 |
| 4" | 72.1 | 3.35 | |

TABLE 6-continued

NMR assignment table

| Carbon number | Chemical shift of $^{13}$C (ppm) | Chemical shift of $^1$H (ppm) | Spin coupling constant J(Hz) |
|---|---|---|---|
| 5″ | 79.9 | 3.36 | $J_{5″,6″}$ = 5.3, 1.4 |
| 6″ | 62.6 | 3.62, 3.81 | $J_{6″,6″}$ = 12.1 |

EXAMPLE 3

Antioxidative Activity Measurement by DPPH Radical Scavenging

Antioxidative activity was evaluated with the use of a stable-radical diphenyl-p-picrylhydradil (DPPH)/ethanol solution. 400 μl of a sample/methanol solution was mixed with 1600 μl of 250 mM acetate buffer (pH=5.5) and 1200 μl of ethanol, at a different concentration, followed by preincubation at 30° C. for 5 minutes. Then, 800 μl of a 500 μM DPPH/ethanol solution was added to each resulting solution, followed by mixing. Each resultant was allowed to stand at 30° C. for 30 minutes, followed by measurement of absorbance at 517 nm. α-tocopherol was also subjected to the same operation. The obtained solution was thus designated as a positive control. A blank solution used was prepared by the same operation with the use of methanol instead of a sample solution. Based on absorbances measured, radical scavenging rates were calculated based on the following equation.

Scavenging rate(%)=(1−[Absorbance of a sample]/[Absorbance of a blank])×100        [Equation 1]

The concentration of a sample solution was changed stepwise for the measurement of the aforementioned scavenging rate. As a result, the concentration of a sample solution at which the DPPH radical scavenging rate was 50% was obtained so as to be designated as the DPPH radical 50% scavenging concentration. The lower such value, the higher the radical scavenging capacity.

Table 7 shows 50% inhibition concentrations of the product of the present invention and α-tocopherol.

The product of the present invention exhibited radical scavenging activity comparable to or exceeding that of α-tocopherol. Thus, the product of the present invention can be expected to have an antioxidative effect comparable to or exceeding that of α-tocopherol.

TABLE 7

| DPPH radical 50% scavenging concentration | |
|---|---|
| α-tocopherol | 0.127 mg/mL |
| Product of the present invention | 0.080 mg/mL |

EXAMPLE 4

α-Glucosidase Inhibitory Activity

A yeast-derived reagent (Wako Pure Chemical) was used as an α-glucosidase. The reagent was dissolved in 10 mM phosphate buffer (pH 7.0) containing 0.2% bovine serum albumin.

For comparison with the polyphenol glycoside of the present invention, taxifolin (Sigma, catalog no. T4512), isoquercitrin (Kanto Chemical Co., Inc., catalog no. 20311-96), quercitrin (Wako Pure Chemical Industries, Ltd., catalog no. 174-00031), and acarbose (LKT Laboratories, Inc., catalog no. A0802) were used.

In the experiment, 0.25 mL of 100 mM phosphate buffer, 0.25 mL of each sample solution at a different concentration, and 0.125 mL of a maltose aqueous solution serving as a substrate at a concentration of 10 mg/mL were mixed, followed by heating at 37° C. for 5 minutes. Then, 0.125 mL of an α-glucosidase solution was added thereto, followed by enzyme treatment at 37° C. for 60 minutes. As a reaction termination solution, 0.5 mL of a 0.2 M sodium carbonate solution was added to each resultant, followed by mixing. The glucose concentration of each reaction solution was measured using Glucose CII-Test Wako (Wako Pure Chemical). An inhibition rate (%) was calculated based on a proportion of the glucose concentration of a solution to which a sample had been added to the glucose concentration of a blank solution to which no sample had been added. Then, the concentration of each sample at which 50% enzyme activity was inhibited was calculated based on such inhibition rate derived from the concentration of the sample, followed by comparison. Table 8 shows the measurement results.

The product of the present invention was confirmed to have enzyme inhibitory activity several times stronger than that of isoquercitrin (compound having a structure in which glucose is bound to quercetin) and that of taxifolin (compound having a structure in which glucose is removed from the structure of polyphenol glycoside of the present invention). The results suggest that the polyphenol glycoside of the present invention have strong α-glucosidase inhibitory activity due to a novel binding mode between polyphenol and sugar.

TABLE 8

| 50% α-glucosidase inhibitory activity concentrations of samples | |
|---|---|
| Sample name | 50% α-glucosidase inhibition concentration (mM) |
| Product of the present invention | 0.164 |
| Taxifolin | 0.892 |
| Isoquercitrin | 0.727 |
| Quercitrin | 2.532 |
| Acarbose | 1.256 |

All publications, patents, and patent applications cited herein are incorporated herein by reference in their entirety.

The invention claimed is:

1. An isolated compound represented by the following formula (I):

or a salt thereof.

2. A method for producing the isolated compound represented by formula (I) according to claim 1, comprising isolating the compound from an acerola fruit or a processed product thereof.

3. A glucosidase inhibitor comprising, as an active ingredient, an isolated compound represented by formula (I):

or a salt thereof in an amount effective for providing glucosidase inhibitory activity.

4. An antioxidant comprising, as an active ingredient, an isolated compound represented by formula (I):

or a salt thereof in an amount effective for providing antioxidative activity.

5. A food comprising an isolated compound represented by formula (I):

or a salt thereof in an amount effective for providing glucosidase inhibitory activity or antioxidative activity.

6. A cosmetic comprising an isolated compound represented by formula (I):

or a salt thereof in an amount effective for providing antioxidative activity.

7. A skin preparation for external use comprising an isolated compound represented by formula (I):

or a salt thereof in an amount effective for providing antioxidative activity.

8. An isolated mixture consisting essentially of a compound represented by formula (I):

or a salt thereof, and acerola-polyphenols.

* * * * *